United States Patent [19]

Javelle

[11] Patent Number: 4,553,546
[45] Date of Patent: Nov. 19, 1985

[54] ASSEMBLY FOR REGULATING THE ENERGY CIRCULATING IN THE MERIDIANS AND METHOD OF USE

[76] Inventor: Edmond Javelle, Résidence Méridien A/21 20 rue Gembloux, 59240 Dunkerque, France

[21] Appl. No.: 604,121

[22] Filed: Apr. 24, 1984

Related U.S. Application Data

[63] Continuation of Ser. No. 343,711, Jan. 28, 1982, abandoned.

[30] Foreign Application Priority Data

Feb. 5, 1981 [FR] France .............................. 81 02792

[51] Int. Cl.⁴ .............................................. A61N 5/00
[52] U.S. Cl. ................................................... 128/395
[58] Field of Search ............................ 128/395–398, 128/303.1, 907, 735

[56] References Cited

U.S. PATENT DOCUMENTS

| 4,112,923 | 9/1978 | Tomecek ...................... 128/395 X |
| 4,232,678 | 11/1980 | Skovajsa ............................ 128/395 |
| 4,279,254 | 7/1981 | Boschetti et al. .................. 128/395 |

FOREIGN PATENT DOCUMENTS

| 2371935 | 7/1978 | France ................................ 128/395 |
| 997670 | 7/1965 | United Kingdom ............... 128/735 |

Primary Examiner—Lee S. Cohen
Attorney, Agent, or Firm—Kerkam, Stowell, Kondracki & Clarke

[57] ABSTRACT

The invention relates to an assembly for regulating the energy circulating in the meridians.

It is characterized in that the said assembly comprises two identical apparatuses, each designed only to emit the said wave (13) exclusively, at full power and at two pulse frequencies which only vary at a ratio of one to two.

Application to acupuncture.

2 Claims, 3 Drawing Figures

ASSEMBLY FOR REGULATING THE ENERGY CIRCULATING IN THE MERIDIANS AND METHOD OF USE

BACKGROUND OF THE INVENTION

This is a continuation of application Ser. No. 343,711 filed on Jan. 28, 1982, and now abondoned.

The invention relates to an assembly for regulating the energy circulating in all the meridians of the human body by means of an infrared wave chopped into sections transmitted at predetermined frequencies to be used entirely for application in the art of acupuncture and in this respect as a substitute for the conventional means used up to now, i.e. needles.

Apparatus for transmitting an infrared wave chopped into sections transmitted at predetermined frequencies is already known (French Patent Specification No. 2279253).

In this apparatus the wave cut up in this way is transmitted by an electroluminescent diode which, in response to a sequence of electrical pulses, converts this electrical energy into an electromagnetic wave which, in accordance with its length, may be located in the infrared spectrum (starting from eight hundred nanometers).

In this known apparatus the diode used is, for example, a gallium arsenide diode to which the electrical pulses are supplied by an oscillator circuit.

By determining the chopping frequency of the infrared wave and the duration of each section, the frequency and the duration of the electrical pulses supplied to the diode may, by means of divider and/or forming circuits of any known type, vary to a large extent so that the infrared wave may be transmitted both in a practically continuous manner and may be transmitted during instants varying in length and varying in spacing.

The apparatus of the invention is for exclusive application to conventional acupuncture, wherein by means of the suitable utilisation of the known points of acupuncture of the meridians in order to provide not only an anatomical and histological specificity but in particular a specificity of action, it therefore enables the energy circulating in all the meridians of the human body to be regulated whilst respecting the overall energy rules which are different from auriculotherapy. The apparatus acts at the point of acupuncture by stimulation or even by dispersion according to the aim of the treatment and the type of disorder to be treated.

Parallel to treatment by conventional acupuncture, in accordance with which the energy circulation is regulated by acting on the above-mentioned points which are therefore distributed over almost the entire human body, treatment by auriculotherapy in accordance with which certain disorders are treated by acting on points located at the external ear where the reflex zones of each part of the body are located, whether this involves parts of limbs, organs, viscera etc., rather than acting directly on meridian paths which lead to impact with the most important seats of energy within the organism.

In both of these methods, treatment is carried out conventionally by means which contact the points in question.

This conventional physical contact is provided by needles which are a serious handicap in certain uses, i.e. the pain caused thereby, fear of injections, in particular on the part of children, or the risk of infection caused by puncturing of the skin, or the risk of perforation of serous membranes, vascular and nerve sheaths etc.

An apparatus for diagnosis and treatment which replaces physical contact with a simple projection onto a given reflex zone of an infrared wave chopped in accordance with a particular predetermined frequency (French Patent Specification No. 2371935) has already been used in auriculotherapy.

Each reflex zone only reacts normally to a chopping frequency which is related to it and this reaction is shown in the form of an autonomous vascular signal shown by a pulse variation.

In order to reach a diagnosis a low power is used in order to prevent attendant effects and the wave is projected onto a first zone at a chopping frequency which may be any frequency on commencement and which is adjusted until the autonomous vascular signal appears.

In the absence of any reaction, the operation is carried out again with a frequency belonging to a new zone which is projected onto the other zones.

The possible appearance of the autonomous vascular signal in one of these other zones which therefore reacts at a frequency which is "parasitic" for it then enables, with reference to the value of the frequency and the zone in which the reaction has abnormally appeared, the diagnosis, with a large degree of accuracy, of a disorder for whose treatment the corresponding reflex zone is also subjected to an infrared wave whose power is in this case increased to a value which is sufficient to provide curative effects and whose chopping is carried out in accordance with the so-called "parasitic" frequency rather than in accordance with the normal frequency for the reflex zone in question.

One of th drawbacks of this method using the reflex zones lies in that, in addition to the non-negligible time loss for the operator, the parasitic zones often have to be re-monitored and treatment recommenced.

It was thought that it would be possible to envisage projection of these reflex zones of the external ear at the level of the surface of the body. However it was shown in practice that this transposition was not valid and that the manipulation of the energy of the meridians using these concepts often led to effects which were harmful or opposite to the therapeutic aim desired.

In effect this proved to be incompatible with the acupunctural dynamics of manipulation of the energy at the meridians which obeys its own well-defined laws within the framework of the overall energy laws of acupuncture, in accordance with the inventor.

Thus in the case of a meridian circulating in a defined bodily segment there is no correspondence at any level of the different specific points of acupuncture selected along this meridian and the somatotopy of this segment over the reflex zone of the external ear with respect to the chopping of the frequency of the wave used.

This is therefore the discovery of the invention, showing that as dangerous actions may even aggravate the disorders which may arise from the direct transposition of the method of auriculotherapy described above to the energy manipulation at the energy meridians or channels in each of which there circulate relatively specific energies which carry messages and accurate commands for the body as a whole.

It has therefore been noted that it was not of use to resort to apparatus transmitting a wave at several power levels as in order to cause energy to circulate through the meridians it is useless and even dangerous to ascertain in which frequential reflex zone of the points one is located by correlation with somatotopy at the ear.

In effect to act otherwise would lead to diffractions varying in extent and varying in localisation of the energy circulating within the meridians and consequently both to an insufficient therapeutic effect and to harmful effects which may be serious.

In addition it has been noted that it was erroneos, in contrast to the teaching provided by the prior art, to use apparatus transmitting a wave chopped at frequencies which, irrespective of their actual values, are increasingly numerous, and in particular seven frequencies varying in particular at a ratio of one to sixty-four for certain gallium arsenide diode devices (French Patent Specification Nos. 2371935 and 2420352) and sixteen frequencies varying at a ratio of one to eight hundred in the case of other laser effect diodes (French Patent Specification No. A-2390968).

Moreover, the apparatus used in auriculotherapy is difficult to adjust and includes frequencies which are dangerous in their practical application. It should be borne in mind that the resonance frequencies of various zones of the external ear are very numerous and are distributed in very large proportions and more precisely in a ratio of one to sixty-four.

The auriculotherapy apparatus should therefore provide a range of frequency regulation which is as least as great, and the infrared radiation chopped in this way should be able to be transmitted both at low and high power for diagnosis and treatment respectively.

SUMMARY OF THE INVENTION

This has nothing to do with the invention which has enabled the selection of two pulse frequencies alone for practical use in acupuncture and which vary at a ratio of one to two.

One of these frequencies serves to disperse the energy circulating in the meridians and the other to stimulate or tone it.

In effect, contrary to presumptions which indicate that the specific points of the meridians may only react at the widely varying frequencies used in auriculotherapy, the inventor has observed that the general rules of energy circulation do not correspond to those of auriculotherapy and has been able to isolate from the large range described above the two single frequencies which are useful and sufficient to treat all the disorders which are in fact linked to a disturbance of the general energy circulation. In addition, using this method, the effectiveness of the treatment was permanent, whilst the use of other frequencies had no effect, or an insufficient or harmful effect, causing for example a diffraction of the energy, or wasting this precious energy and leading to an unsatisfactory result.

The other object of the invention is to provide an assembly of small dimensions which is very simple to adjust and responds to the single possible frequency ranges in the energy manipulation in acupuncture at the meridians, which frequencies have been researched in order to provide a maximum efficiency which is rapid and harmless and capable of replacing the conventional needles.

Moreover the diode has been carefully selected from tests with patients in which the meridian circuits were observed with the slightest stimulation, which has enabled the selection of the most efficient diode, as well as the single frequencies of use possible bearing in mind the rapidity of obtaining results, the more or less marked rapidity of the resolution of the symptoms in accordance with the type of diode used and the choice of the matching frequencies.

The radiation transmitted by certain of these diodes may also be badly tolerated, whereas stimulation during acupuncture should never be unpleasant.

For this reason as well the diode has been suitably selected, bearing in mind differences in depth of energy in Yin and Yang zones.

It has also been selected as a function of a certain diameter enabling a certain degree of action even when the operator has made an error in the range of one millimeter in the anatomical or topographical determination of the point of acupuncture whose specificity is essential.

For this purpose, the invention relates to an assembly of the type described above, characterised in that the said assembly comprises two identical apparatuses, each designed only to transmit the said wave exclusively at full power and at two pulse frequencies which only vary at a ratio of one to two.

BRIEF DESCRIPTION OF THE DRAWING

The invention is illustrated in the following description given by way of non-limiting example, with reference to the attached drawings which show in diagram form.

DESCRIPTION OF THE PREFERRED EMBODIMENT

Figure 1:
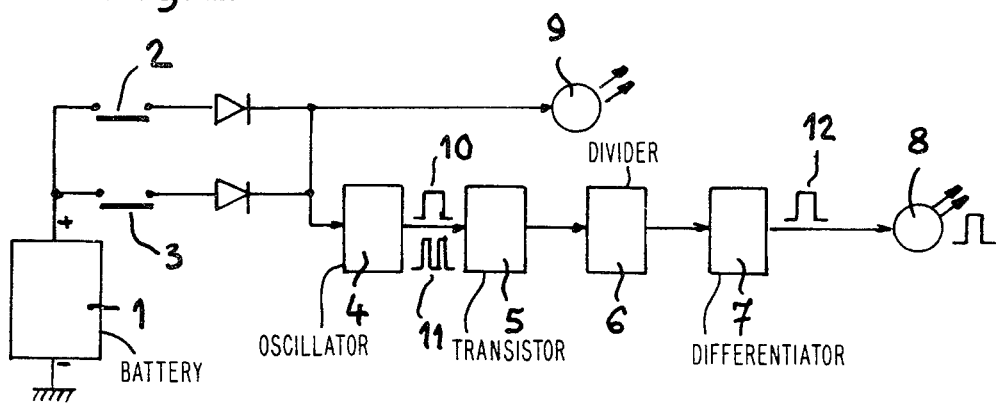
FIG. 1: the outline of the apparatus.
Figure 2:
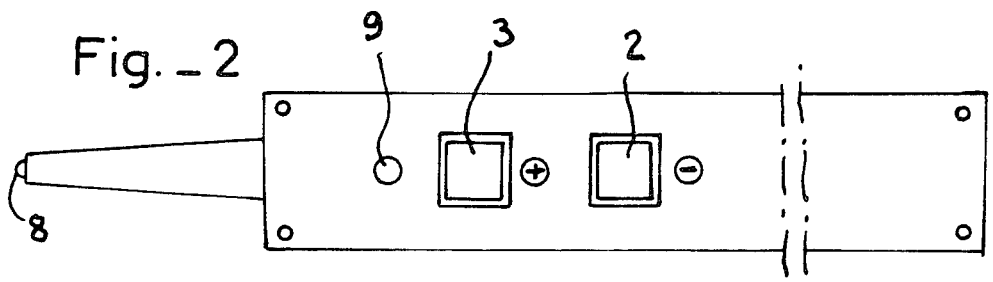
FIGS. 2 and 3: an apparatus seen in front and profile views.
Figure 3:
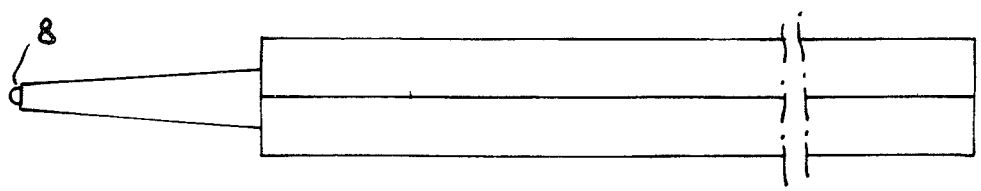

As mentioned above, the assembly comprises two identical apparatuses each provided with an electroluminescent diode 8 (such as the diode distributed under the references DEL: Ga As EPITAXIE) whose particular feature is to transmit radiation 13 in the infrared range centered on 930 nm (i.e. 9,300 angstroms).

The infrared emission 13 is radiated, intermittently, at the frequency depending on the control button 2 or 3 selected, i.e. a button 2 called dispersion button and a button 3 called toning button, which cause the oscillator 4 to operate at base frequencies 10–11 which differ as a result of the actuation of different "resistor-capacitor" networks, determined such that the said base frequencies are in a ratio of one to two with respect to one another.

The base frequency 10 corresponding to the dispersion button 2 is 4650 Hz plus or minus 10% and the base frequency for the toning button 3 is 9300 Hz plus or minus 10%, which frequencies are, in the inventor's opinion, the only frequencies which may be used in acupuncture according to that selected diode.

A transistor 5 enables the pulses 10 or 11 to be calibrated before they are divided by a divider circuit 6.

After the divider, a differentiator 7 mainly comprising a transistor, enables correct calibration of chopping to the required frequencies with the adequate cyclical ratio.

The diode 8 is therefore supplied with electrical pulses 12
  in the case of dispersion, every 1720 microseconds,
  in the case of toning, every 860 microseconds, and the duration of conduction of the diode is 40 nanoseconds.

All these values may obviously vary by plus or minus 10%.

An indicator light 9 constituted by an electroluminescent diode transmitting in the visible spectrum indicates actuation of the battery 1.

The light intensity of this indicator light 9 itself enables evaluation of the wear of this battery 1.

The assembly also also comprises an infrared radiation receiver (not shown) in order to sense and monitor with accuracy the condition of the battery 1 and the transmission quality of the infrared diode 8.

In order to achieve a suitable balance of energy for the individual, to regulate the needs of his body in all cases, the apparatus, in a characteristic manner, may only emit at two pulse frequencies:

one for dispersing energy and for preventing it from following its normal path and therefore to cause it to take eventually a derivatory path, the other for stimulating it, and for causing it to follow its normal path more rapidly, or even for further increasing the physiological effect of the point within the meridian.

In this respect the inventor draws attention to a principal concept currently used in acupuncture: the concept of the inductive point and the directive point.

As the energy is derived from numerous meridians in the same way as actual electronic networks, there are numerous points of intersection and numerous points having multiple physiological characteristics. The energy must therefore be guided through the control points and through the points of intersection as otherwise, when it reaches these points, it would no longer know in which direction to go.

The energy must therefore be caused to flow in a particular direction, and this has led to the use in a simultaneous manner of two points responding to this concept of the inductive point and the directive point, this being of particular importance in practical applications.

For this purpose, use must therefore be made at all times of an assembly formed from two apparatuses, not only in order to satisfy this concept but also so as to be able to act in a symmetrical manner on the body energy and to suitably balance this energy.

Thus, before any treatment by acupuncture it is necessary to carry out a general energy re-balancing operation which makes the simultaneous and symmetrical use of two apparatuses at the points of acupuncture obligatory.

It has therefore been shown that this assembly of apparatus is designed quite differently with respect to its practical applications, from auriculotherapy which must satisfy different rules.

It may be applied in practice immediately in an extremely effective manner for all ages without pain and without any harmful effect by the accurate choice of frequencies which one may finally envisage extending by approximately 10%.

It is obvious that the invention is not limited to the above description and that it may include numerous variants, not only with respect to its external aspect and the diode used and with this the parameters characterising the pulses, i.e. their frequency, amplitude and duration, but also with respect to the mode of transmission of the wave, either directly by lasers or laser diodes, or via light conductors such as optical fibres.

I claim:

1. Applicator for application to known points of acupuncture for regulating the energy circulating in the meridians of the human body in the sense of dispersion or stimulation of the energy in accordance with disorders to be treated and of the type employing radiation from an emitting diode, said applicator comprising:

a body portion;

an emittting diode carried by the body portion;

an electrical circuit means in said body portion for supplying energizing pulses to said diode such that said diode emits a chopped wave; and the pulses being of a substantially constant amplitude and at either one of two frequencies which are related to each other in substantially a one-to-two ratio, one of the pulse frequencies being for dispersion and the other of the pulse frequencies being for stimulation, and wherein said circuit means supplies said diode with pulses only at:

a dispersion frequency with a pulse repetition interval of 1720 microseconds plus or minus ten per cent, and a stimulation frequency with a pulse repetition interval of 860 microseconds plus or minus ten per cent.

2. A method of treatment of a living body for regulating the energy circulating in meridians of the body in the sense of dispersion or stimulation of the energy in accordance with disorders to be treated and of the type of method employing radiation from an emitting diode applied to acupuncture points, the method comprising the steps of:

(a) placing two applicators in energy transfer relationship to acupuncture points of the body, each applicator comprising:

a body portion;

an emitting diode carried by the body portion;

an electrical circuit means in said body portion for supplying energizing pulses to said diode such that said diode emits a chopped wave, and the pulses being of a substantially constant amplitude and at either one of two frequencies which are related to each other in substantially a one-to-two ratio, one of the pulse frequencies being for dispersion and the other of the pulse frequencies being for stimulation, and wherein said circuit means supplies said diode with pulses only at:

a dispersion frequency with a pulse repetition interval of 1720 microseconds plus or minus ten percent, and a stimulation frequency with a pulse repetition interval of 860 microseconds plus or minus ten percent; and (b) simultaneously applying energy to the body from said two applicators so as to balance body energy, each applicator applying energy at said dispersion frequency or at said stimulation frequency.

* * * * *